United States Patent [19]

Bouffard et al.

[11] Patent Number: 4,816,578

[45] Date of Patent: Mar. 28, 1989

[54] PROCESS FOR THE STEREOCONTROLLED SILYLOXYETHYLATION OF AZETIDINONES

[75] Inventors: F. Aileen Bouffard, Scotch Plains; Thomas N. Salzmann, Plainfield, both of N.J.

[73] Assignee: Merck & Co., Inc., Rahway, N.J.

[21] Appl. No.: 165,364

[22] Filed: Feb. 26, 1988

Related U.S. Application Data

[63] Continuation of Ser. No. 879,549, Jun. 24, 1988, abandoned, which is a continuation of Ser. No. 611,301, May 17, 1984, abandoned.

[51] Int. Cl.$^4$ .......................... C07F 7/18; C07F 7/10; C07B 41/02; C07B 41/04
[52] U.S. Cl. .................................. 540/200; 540/360; 540/300; 540/310
[58] Field of Search ................................ 540/200, 360

[56] References Cited

U.S. PATENT DOCUMENTS 4,223,038  9/1980  Smale .......................... 260/245.2 T
4,383,945  5/1983  Hashimoto .................. 260/245.2 T

OTHER PUBLICATIONS

Brook, J. American Chem Society 80, 1886 (1958).
Brook, J. Amer Chem Society 81, 981 (1959).
F. Aileen Bouffard et al., J. Organic Chemistry 45, 1130–1135 (1980).
I. Shinkai et al, Tetrahedron Letters, 23, 4899–4902 (1982).
S. R. Wilson et al., J. Org. Chem., 1982, 47, 747–748.
F. A. Bouffard et al., J. Org. Chem., 45, (1980) 1130–1135.
F. A. Bouffard et al. J. Org. Chem., 46, 2208–2212 (1981).
A. G. Brook et al., J. Am. Chem. Soc, 89 (1967) 431–434.
E. J. Corey et al., J. Am. Chem. Soc. 89 (1967) 434–436.
M. Miyoshita et al., J. Chem. Soc. Chem, Commun. (1982) 1354–1356.
P. J. Reider et al. Tet. Letters, (1982) vol. 23, 2293–2295.
J. d'Angelo et al. Tet. Letters, (1983), pp. 1403–1406.
A. Yoshida et al., Chem. Pharm. Bull., vol. 28, pp. 2899–2909 (1981).
A. Martel, Can. J. Chem., vol. 61, pp. 613–618 (1983).
I. Shinkai; et al., Tet. Letters vol. 23, pp. 4899–4902 (1982).
F. Pecquet et al, Tet. Letters (1982), 2777–2780 (1982).
A. G. Brook, Accounts Chem. Res., vol. 7, pp. 77–84 1974).
A. B. Hamlet et al., Can. J. Chem, 61, pp. 411–415 (1983).

Primary Examiner—Mark L. Berch
Attorney, Agent, or Firm—Robert J. North; Hesna J. Pfeiffer

[57] ABSTRACT

A stereospecific process for preparing 3-trans-R-trisubstituted silyloxyethyl substituted azetidinones useful as intermediates for preparing penems and carbapenems is provided wherein a 3-unsubstituted azetidinone is treated with a strong base and a trisubstituted silylmethyl ketone to form 3-trans-S-[1-trisubstituted silyl-1-hydroxy]ethylazetidinone followed by rearrangement of this resulting carbinol by treatment with an alkali metal alkoxide and a proton source.

7 Claims, No Drawings

PROCESS FOR THE STEREOCONTROLLED SILYLOXYETHYLATION OF AZETIDINONES

This application is a continuation of Ser. No. 879,549, filed June 24, 1988, abandoned, which is a continuation of Ser. No. 611,301, filed May 17, 1984, abandoned.

BACKGROUND OF THE INVENTION

The invention concerns the preparation of azetidinones useful as intermediates for preparing penems and carbapenems.

Carbapenems (I) and penems (II) are classes of antibiotic compounds characterized by the formulae

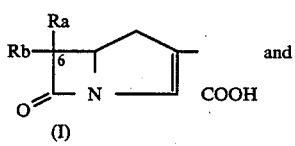 and

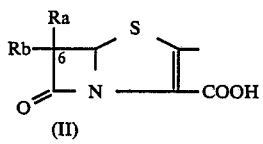

Compounds of special interests are I or II when the substituent $CH_3$—CHOH— is in the six position and has a particular isomer configuration. An example of such a compound is thienamycin having the formula

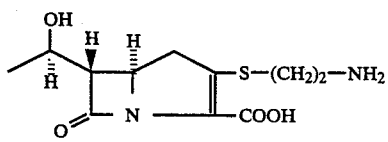

A useful synthesis of a compound such as A requires an intermediate azetidinone of the formula

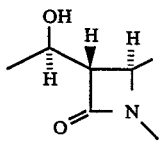

Introduction of the $CH_3$—CHOH—side chain via alkylation of the β-lactam enolate is a direct route to B, however, it suffers from being nonstereospecific. A less direct route to B is a two step sequence involving acetylation of a β-lactam enolate followed by stereospecific reduction of the β-keto lactam product. This reduction requires sophisticated and expensive reducing agents.

The present novel process has been discovered which provides a simpler and more direct route to the B intermediate protected as an O-silyl ether.

SUMMARY OF THE INVENTION

A stereospecific process for preparing a trans-R-substituted azetidinone of the formula

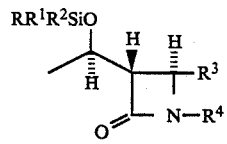

DETAILED DESCRIPTION OF THE INVENTION

An embodiment of the present invention is a process for preparing a trans-R substituted azetidinone of the formula

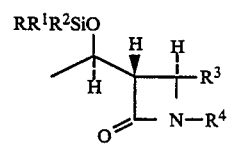

wherein

R, $R^1$ and $R^2$ are independently selected from $C_1$-$C_6$alkyl, aryl and substituted aryl, aralkyl and substituted aralkyl, (typically, R, $R^1$ and $R^2$ are chosen from the group of methyl, ethyl, isopropyl, t-butyl, phenyl and p-methoxyphenyl).

$R^3$ is $C_2$-$C_6$ alkenyl,

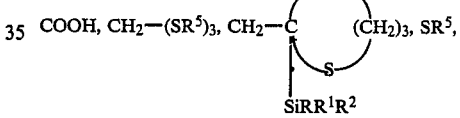

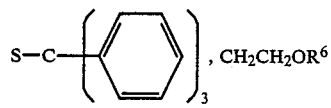

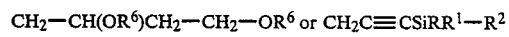

wherein $R^6$ is a protecting group such as alkyl, benzyl, triorganosilyl when organo is $C_1$-$C_6$alkyl tetrahydropyrroyl and the like and $R^5$ is selected from $C_1$-$C_6$alkyl, aryl or substituted aryl, aralkyl or substituted aralkyl, (typically, $R^5$ is methyl, ethyl, propyl, phenyl, benzyl, p-methoxyphenyl or p-methoxybenzyl.)

$R^4$ is $SiRR^1R^2$, $C(COOR^7)=C(CH_3)_2$ H or $C(COOR^7)=P(C_6H_5)_3$ wherein $R^7$ is H, $C_1$-$C_6$ alkyl, $CH_2CCl_3$, $(CH_2)_2Si(CH_3)_3$, benzyl, nitrobenzyl, $CH_2COCH_3$, $CH_2$—CH=$CH_2$, $CH_2OCOCH_3$ or $SiRR^1R^2$, and $R^3$ and $R^4$ when joined are —$(CH_2)_2$—O—$C(CH_3)_2$—, —$S(O)_2C(CH_3)_2CH(COOR^7)$—, —$C(R^5)_2CH_2OC(CH_3)_2$— or —$SC(R^8)=C(COOR^7)$— wherein $R^7$ as defined above:

which comprises treating a compound having the formula

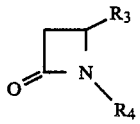

with a strong base followed by a methyl silyl ketone having the formula

to obtain the trans-S substituted azetidinone having the formula

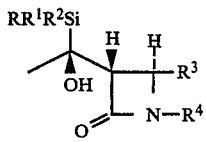

and rearranging V to obtain III.

The process is illustrated by the following reaction equations n

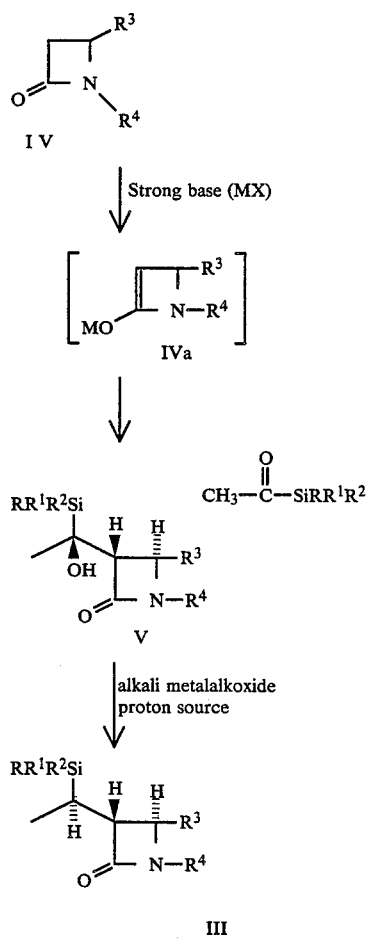

The carbinol V is prepared by treatment of the azetidinone (IV) in an inert solvent with a strong base to form the anion (IVa) followed by reaction of the anion mixture with the methyl silyl ketone. The solvent may be tetrahydrofuran, diethyl ether, dimethoxyethane and the like. The base may be a lithium dialkylamide, a lithium disilylamide, an alkyl lithium or an aryl lithium. The silyl group of the methyl silyl ketone may be any triorganosilyl radical such as trimethyl, tert-butyldimethyl, tert-butyldiphenyl, triisopropyl, diphenylmethyl and the like. The process is carried out with cooling (e.g. −78° to 0° C.). The preferred solvent is tetrahydrofuran and the preferred base is lithium diisopropylamide. General procedures for aldol reactions of this type with acetaldehyde are described in *Journal of Organic Chemistry,* 45, 1130–1135 (1980) and *Tetrahedron Letters,* 23, 4899–4902 (1982).

The rearrangement of the carbinol (V) to the alkoxy silane is accomplished by treatment of the carbinol with an alkali metal alkoxide and a proton source. The solvent may be tetrahydrofuran, diethyl ether, dimethoxyethane and the like. The preferred solvent is tetrahydrofuran. The preferred alkali metal alkoxide is potassium tert-butoxide in the presence of tert-butyl alcohol as the proton source. The process is carried out with cooling (e.g. −40° to 0° C.).

Alternatively to the two-step sequence, the process can be carried out in one reaction vessel without isolation of the carbinol V. The carbinol, as its lithium salt, is treated directly with the alkali metal alkoxide and the proton source.

Examples illustrating the present process follow.

EXAMPLE 1

Preparation of (6RS,7SR)-7-[(SR)-1-(tert-Butyldimethylsilyl)-1-hydroxyethyl]-2,2-dimethyl-1-azabicyclo[4.2.0]octan-8-one

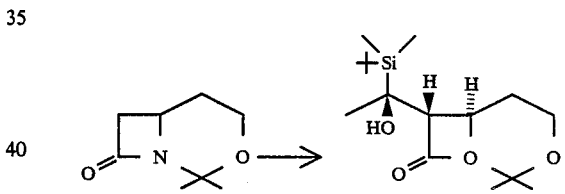

A solution of (6RS)-2,2-dimethyl-1-azabicyclo[4.2.0]octan-8-one (104 mg, 0.671 mmol) in 1 ml of tetrahydrofuran is added to a solution of lithium diisopropylamide (0.705 mmol made from 99 μl of diisopropylamine and 320 ml of a 2.2M solution of n-butyllithium in n-hexane) in 4 ml of tetrahydrofuran at −78° C. The enolate solution is aged for a period of 12 minutes and then methyl tert-butyldimethylsilyl ketone is added and stirring is continued for a period of 19 minutes. The reaction mixture is poured into a separatory funnel containing 5 ml of a saturated aqueous solution of ammonium chloride and shaken. The mixture is extracted with 10 ml of diethyl ether and the ether solution is dried over magnesium sulfate. Removal of the solvents in vacuo gives 206 mg of a colorless oil. Plate-layer chromatography of this material on silica gel (1:1 ethyl acetate/cyclohexane) provides 171 mg (81%) of (6RS,7SR)-7-[(SR)-1-(tert-butyldimethylsilyl)-1-hydroxyethyl]-2,2-dimethyl-1-azabicyclo[4.2.0]octan-8-one ($R_f$ 0.41–0.65): m.p. 60°–3° C. (recrystallized from pentane); ir (CH$_2$Cl$_2$) cm$^{-1}$ 3608 (br), 1739; nmr (CDCl$_3$) δ0.03 (s, 3), 0.06 (s, 3), 1.00 (s, 9), 1.34 (s, 3), 1.42 (s, 3), 1.76 (s, 3), 1.85 (m, 2), 3.24 (d, 1, J=1.9 Hz), 3.40 (ddd, 1, J=1.9, 4.9 and 10.6 Hz), 3.88 (m, 2); ms m/e 314 (M+1)$^+$, 298, 198; anal. (C$_{16}$H$_{31}$NO$_3$Si)C, H, N.

EXAMPLE 2

Preparation of (6RS,7SR)-7-[(RS)-(tert-Butyldimethylsilyloxy)ethyl]-2,2-dimethyl-1-azabicyclo[4.2.0]octan-8-one

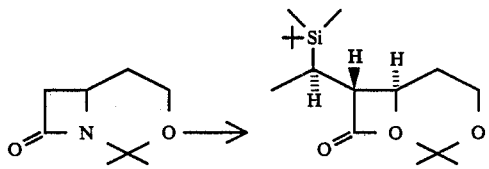

A solution of (6RS)-2,2-dimethyl-1-azabicyclo[4.2.0]octan-8-one (93 mg, 0.600 mmol) in 1 ml of tetrahydrofuran is added to a solution of lithium diisopropylamide (0.660 mmol made from 92 μl of diisopropylamine and 300 μl of 2.2M n-butyllithium in n-hexane) in 4 ml of tetrahydrofurn at −78° C. After stirring for a period of 7 minutes, methyl tert-butyldimethylsilyl ketone (98 mg, 1.03 mmol) is added neat. Stirring is continued for an additional 7 minutes and then 660 μl of a 1M solution of potassium tert-butoxide in tert-butanol is added. The dry ice/acetone cooling bath is replaced with an ice water bath and stirring is continued for a period of 20 minutes. The reaction mixture is poured into a separatory funnel containing 5 ml of a saturated aqueous solution of ammonium chloride and shaken. The mixture is extracted with 10 ml of diethyl ether. The ether solution is washed with water (3×) and brine and dried over magnesium sulfate. Removal of the solvent in vacuo gives 151 mg of a colorless oil which by nmr is a 4:1:95 mixture of cis/trans-S*/trans-R* O-silyl ethers. Plate-layer chromatography on silica gel (1:2 ethyl acetate/cyclohexane) provides 135 mg (72% yield) of crystalline (6RS,7SR)-7-[(RS)-(tert-butyldimethylsilyloxy)ethyl]-2,2-dimethyl-1-azabicyclo[4.2.0]octan-8-one: ir (CH$_2$Cl$_2$) cm$^{-1}$ 1730; nmr (CDCl$_3$) 0.06 (s, 6), 0.86 (s, 9), 1.18 (d, 3, J=6.2 Hz), 1.39 (s, 3), 1.73 (s, 3), 1.83 (m, 2), 2.77 (dd, 1, J=1.9 and 4.7 Hz), 3.63 (ddd, 1, J=1.9, 4.8 and 10.7 Hz), 3.86 (m, 2), 4.18 (dq, 1, J=4.7 and 6.2 Hz); mass spectrum (EI) m/e 298, 256, 198.

EXAMPLE 3

(3S,4R)-1-(tert-Butyldimethylsilyl)-3-[(R)-1-(tert-butyldimethylsilyloxy)ethyl]-azetidine-2-one-4-carboxylic acid

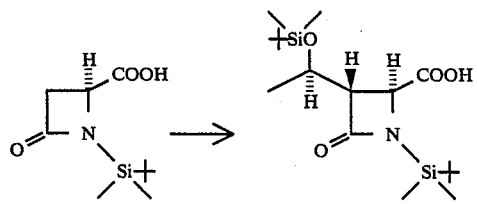

A solution of (S)-N-tert-butyldimethylsilylazetidin-2-one-4-carboxylic acid (200 mg, 0.873 mmol) in 1 ml of tetrahydrofuran is added to a solution of lithium diisopropylamine (1.83 mmol made from 256 μl of diisopropylamine and 871 μl of a 2.1M solution of n-butyllithium in n-hexane) in 2.5 ml of tetrahydrofuran at ca. 3° C. After stirring for a period of 5 minutes, methyl tert-butyldimethylsilyl ketone (152 mg, 0.960 mmol) is added neat. Stirring is continued for a minimum of 10 minutes and then 960 μl of a 1M solution of potassium tert-butoxide in tert-butyl alcohol is added. Stirring is continued for a period of 13 minutes and then the reaction mixture is poured into a separatory funnel containing 5 ml of aqueous citric acid (1:1 citric acid monohydrate/water) and shaken. The mixture is extracted with 10 ml of diethyl ether. The ether solution is washed with water (3×) and brine and dried over magnesium sulfate. Removal of the solvents in vacuo gives 348 mg of crystalline product which by nmr is a 13:87 mixture of trans-S/R O-silyl ethers. Recrystallization from diethyl ether/pentane and chromatography of the crystallization liquor on silica gel eluting with 1% acetic acid/methylene chloride provides (3S,4R)-1-(tert-butyldimethylsilyl)-3-[(R)-1-(tert-butyldimethylsilyloxy)ethyl]-azetidin-2-one-4-carboxylic acid in 77% yield: m.p. 146°-7° C.; ir (Nujol mull) cm$^{-1}$ 1742, 1695; [α]$_D$ +49.1° (c 3,30, CHCl$_3$); nmr (CDCl$_3$) δ0.08, 0.10, 0.19 and 0.27 (4s, 12), 0.90 and 0.98 (2s, 18), 1.24 (d, 3, J=6.25 Hz), 3.34 (dd, 1, J=3.25 and 3.25 Hz), 4.21 (d, 1, J=3.25 Hz), 4.27 (dq, 1, J=3.25 and 6.25 Hz).

Claims to the invention follow.

What is claimed is:

1. A process for preparing a trans-R substituted azetidinone of the formula

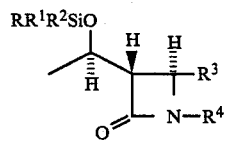

wherein

R, R$^1$ and R$^2$ are independently selected from C$_1$-C$_6$ alkyl, aryl, aralkyl and p-methoxyphenyl R$^3$ is C$_2$-C$_6$ alkenyl, COOH, CH$_2$—C(SR$^5$)$_3$

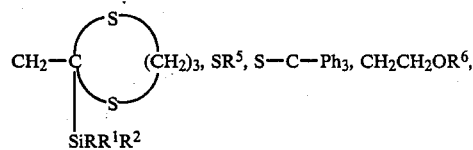

CH$_2$—CH(OR$^6$)CH$_2$—CH$_2$—OR$^6$ or CH$_2$C≡CSiRR$^1$—R$^2$, wherein R$^6$ is a protecting group and R$^5$ is selected from C$_1$-C$_6$alkyl, aryl, aralkyl, p-methoxyphenyl or p-methoxybenzyl, R$^4$ is SiRR$^1$R$^2$, C(COOR$^7$)=C(CH$_3$)$_2$, H or C(COOR$^7$)=P(C$_6$H$_5$)$_3$, wherein R$^7$ is H, C$_1$-C$_6$alkyl, CH$_2$CCl$_3$, (CH$_2$)$_2$Si(CH$_3$)$_3$, benzyl, nitrobenzyl, CH$_2$COCH$_3$, CH$_2$—CH=CH$_2$, CH$_2$OCOCH$_3$ or SiRR$^1$R$^2$, and R$^3$ and R$^4$ when joined are —(CH$_2$)$_2$—O—C(CH$_3$)$_2$—, —S(O)$_2$C(CH$_3$)$_2$CH(COOR$^7$)—, wherein R$^7$ is as defined above; which comprises treating a compound having the formula

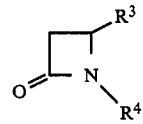

with a strong base followed by a methyl silyl ketone having the formula $$CH_3-COSiRR^1R^2$$

to obtain the trans-S substituted azetidinone having the formula

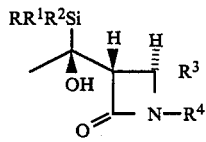

and treating V with an alkali metal alkoxide in the presence of a proton source to obtain III.

2. A compound of the formula

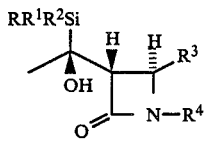

wherein

R, $R^1$ and $R^2$ are independently selected from $C_1$-$C_6$alkyl, aryl and aralkyl $R^3$ is $C_2$-$C_6$alkenyl, COOH, $CH_2$—$C(SR^5)_3$,

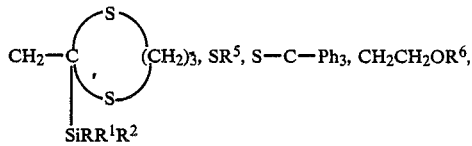

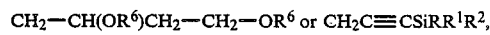

wherein $R^6$ is a protecting group and $R^5$ is selected from $C_1$-$C_6$alkyl, aryl or aralkyl, $R^4$ is $SiRR^1R^2$, $C(COOR^7)=C(CH_3)_2$, H or $C(COOR^7)=P(C_6H_5)_3$, wherein $R^7$ is H, $C_1$-$C_6$alkyl, $CH_2CCl_3$, $(CH_2)_2Si(CH_3)_3$, benzyl, nitrobenzyl, $CH_2COCH_3$, $CH_2$—CH=$CH_2$, $CH_2OCOCH_3$ or $SiRR^1R^2$, and $R^3$ and $R^4$ when joined are —$(CH_2)_2$—O—$C(CH_3)_2$—, —$S(O)_2C(CH_3)_2CH(COOR^7)$—, or —$C(R^5)_2CH_2OC(CH_3)_2$— wherein $R^7$ is as defined above.

3. The process of claim 1 wherein the alkali metal alkoxide is $tBuO^{(-)}K^{(+)}$ and the proton source is t-butanol.

4. The process of claim 1 wherein $R^3$ is COOH and $R^4$ is —Si(t—Bu)(Me)$_2$.

5. The process of claim 1 wherein R, $R^1$, and $R^2$ are selected from methyl, ethyl, isopropyl, t-butyl, phenyl and $R^5$ is selected from methyl, ethyl, propyl, phenyl, benzyl.

6. The composition of claim 2 wherein $R^3$ is COOH and $R^4$ is —Si(t—Bu)(Me)$_2$.

7. The composition of claim 2 wherein R, $R^1$ and $R^2$ are selected from methyl, ethyl, isopropyl, t-butyl, phenyl and p-methoxyphenyl and $R^5$ is selected from methyl, ethyl, propyl, phenyl, benzyl, p-methoxyphenyl or p-methoxybenzyl.

* * * * *